United States Patent
Shin et al.

(10) Patent No.: US 7,875,369 B2
(45) Date of Patent: Jan. 25, 2011

(54) HETEROCYCLE-CONTAINING ORGANOMETALLIC COMPLEX AND ORGANIC LIGHT EMITTING DEVICE INCLUDING THE SAME

(75) Inventors: Jung-Han Shin, Suwon-si (KR); Seung-Gak Yang, Suwon-si (KR); Hee-Yeon Kim, Suwon-si (KR); Chang-Ho Lee, Suwon-si (KR); Hee-Joo Ko, Suwon-si (KR)

(73) Assignee: Samsung Mobile Display Co., Ltd., Suwon-si, Gyeonggi-do (KR)

( * ) Notice: Subject to any disclaimer, the term of this patent is extended or adjusted under 35 U.S.C. 154(b) by 491 days.

(21) Appl. No.: 12/003,467

(22) Filed: Dec. 26, 2007

(65) Prior Publication Data
US 2008/0176105 A1 Jul. 24, 2008

(30) Foreign Application Priority Data
Jan. 18, 2007 (KR) .................... 10-2007-0005813

(51) Int. Cl.
*H01L 51/54* (2006.01)
(52) U.S. Cl. ................ 428/690; 428/917; 313/504; 313/506
(58) Field of Classification Search .............. None
See application file for complete search history.

(56) References Cited

U.S. PATENT DOCUMENTS
6,559,256 B2 5/2003 Holmes et al.

FOREIGN PATENT DOCUMENTS
JP 2004-291253 10/2004

OTHER PUBLICATIONS

Steinhauser et al., Zeitschrift fuer Anorganische and Allgemeine Chemie, (2004), 630 (12), p. 1829-1838.*
Machine translation for JP 2004-291253 A, published Oct. 2004.*
Ludwig, E., et al., "Synthesis and Structure of the Copper Complex 2-(2-Hydroxy-5-methylphenyl-6-(2-hydroxyphenyl)pyridinato(2-) dipyridin-copper(II) and of the free Ligand", Z. anorg. allg. Chem., 622:701-706, (1996) [with English Abstract].
Zhang, Hong-Yu, et al., "Di- and Tetranuclear Metal Complexes with Phenoxo Bridges: Synthesis, Structures, and Photoluminescent and Electroluminescent Properties", Inorg. Chem., vol. 45, No. 4, pp. 1745-1753, (2006).

\* cited by examiner

*Primary Examiner*—Dawn Garrett
(74) *Attorney, Agent, or Firm*—Lee & Morse, P.C.

(57) ABSTRACT

An organometallic complex for a light emitting layer includes a heterocyclic ligand and a bivalent metal bonded to the heterocyclic ligand, wherein the heterocyclic ligand includes a plurality of linked ring structures that include a total of at least 17 carbon atoms and 1 heteroatom, and the linked ring structures have substantially parallel planes.

17 Claims, 1 Drawing Sheet

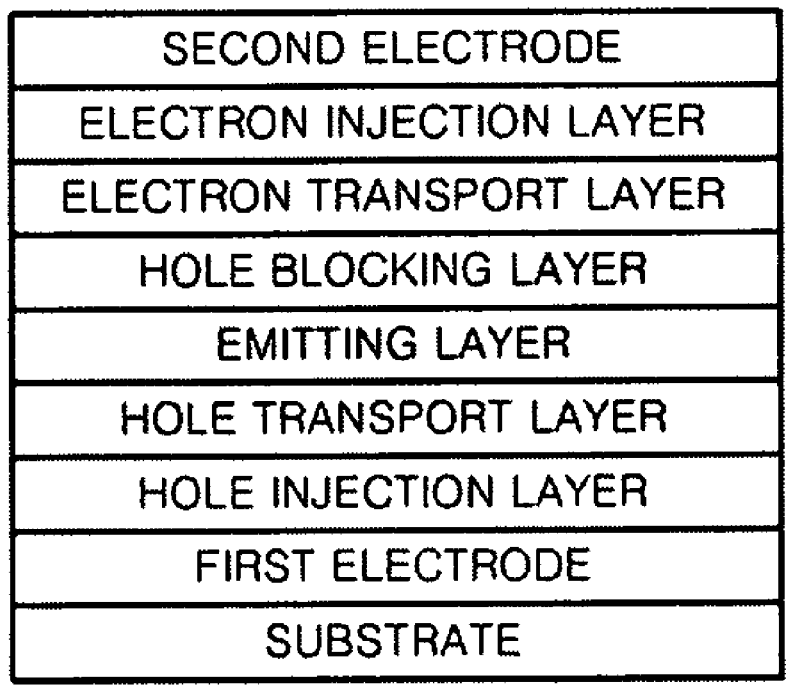

FIG. 1A

| |
|---|
| SECOND ELECTRODE |
| ELECTRON TRANSPORT LAYER |
| EMITTING LAYER |
| HOLE TRANSPORT LAYER |
| FIRST ELECTRODE |
| SUBSTRATE |

FIG. 1B

| |
|---|
| SECOND ELECTRODE |
| ELECTRON INJECTION LAYER |
| ELECTRON TRANSPORT LAYER |
| EMITTING LAYER |
| HOLE TRANSPORT LAYER |
| HOLE INJECTION LAYER |
| FIRST ELECTRODE |
| SUBSTRATE |

FIG. 1C

| |
|---|
| SECOND ELECTRODE |
| ELECTRON INJECTION LAYER |
| ELECTRON TRANSPORT LAYER |
| HOLE BLOCKING LAYER |
| EMITTING LAYER |
| HOLE TRANSPORT LAYER |
| HOLE INJECTION LAYER |
| FIRST ELECTRODE |
| SUBSTRATE |

HETEROCYCLE-CONTAINING ORGANOMETALLIC COMPLEX AND ORGANIC LIGHT EMITTING DEVICE INCLUDING THE SAME

BACKGROUND OF THE INVENTION

1. Field of the Invention

Embodiments of the present invention relate to a heterocycle-containing organometallic complex and an organic light emitting device including the same. More particularly, embodiments of the present invention relate to a heterocycle-containing organometallic complex having improved electrical stability and electron mobility and an organic light emitting device including the same.

2. Description of the Related Art

In general, an organic light emitting device may refer to a flat panel display device employing a light emitting diode (LED) activated by combination of electrons and holes in a light emitting layer thereof, i.e., inorganic or organic. As such, the organic light emitting device may have wide viewing angles, excellent contrast, quick response time, bright colors, and low operating voltage.

The conventional organic light emitting layer of the organic light emitting may include a multi-layered structure, e.g., an emitting layer, a hole blocking layer, an electron injection layer, and so forth, containing an organic material. However, the conventional organic material employed in the organic light emitting layer, e.g., material used to form the hole blocking layer, may require relatively high driving voltage and power consumption, thereby causing faster organic material deterioration, i.e., insufficient lifetime and/or luminous efficiency.

SUMMARY OF THE INVENTION

Embodiments of the present invention are therefore directed to a heterocycle-containing organometallic complex and an organic light emitting device including the same, which substantially overcome one or more of the disadvantages of the related art.

It is therefore a feature of an embodiment of the present invention to provide a heterocycle-containing organometallic complex for a light emitting layer.

It is another feature of an embodiment of the present invention to provide an organic light emitting device with a light emitting layer including a heterocycle-containing organometallic complex.

At least one of the above and other features and advantages of the present invention may be realized by providing a substantially planar organometallic complex for a light emitting layer, including a heterocyclic ligand and a bivalent metal bonded to the heterocyclic ligand. The heterocyclic ligand may include a plurality of linked ring structures that include a total of at least 17 carbon atoms and 1 heteroatom, and the linked ring structures may have substantially parallel planes.

The organometallic complex may be represented by a general Formula 1,

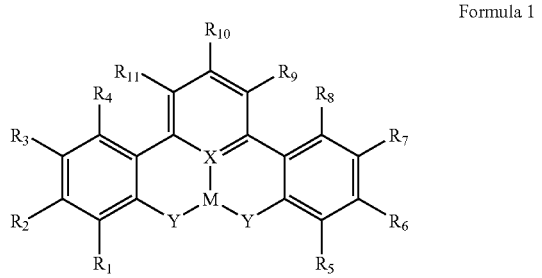

Formula 1 wherein $R_1$ through $R_{11}$ may each independently be a hydrogen atom, a cyano group, a hydroxyl group, a nitro group, a halogen atom, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, or a substituted or unsubstituted C2-C20 hetero ring group; M may be beryllium, magnesium, zinc, calcium, chromium, iron, cobalt, nickel, or copper; X may be nitrogen or phosphorous; and Y may be oxygen or sulfur. At least two of the $R_1$ through $R_{11}$ may be bound to each other to form a ring.

The compound represented by Formula 1 may be any one of compounds represented by general Formulae 2 through 6,

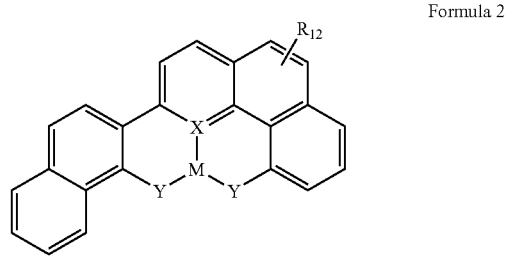

Formula 2

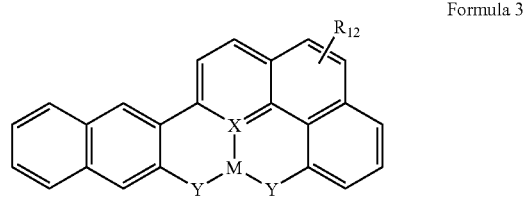

Formula 3

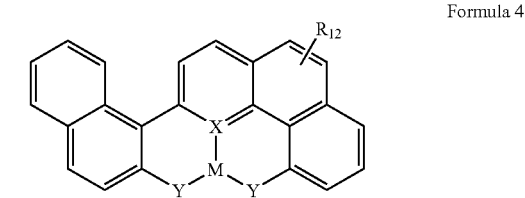

Formula 4

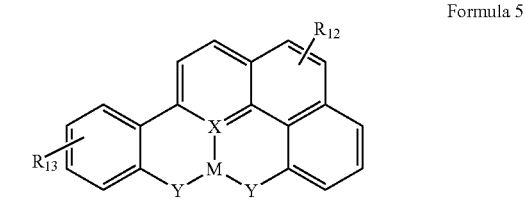

Formula 5

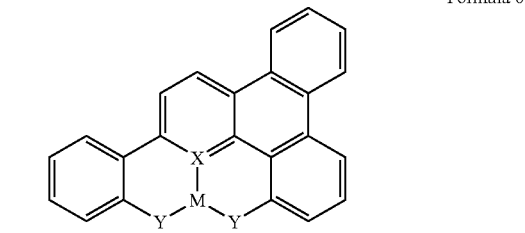

Formula 6 wherein $R_{12}$ and $R_{13}$ may each independently be a hydrogen atom, a cyano group, a hydroxyl group, a nitro group, a halogen atom, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, or a substituted or unsubstituted C2-C20 hetero ring group. Each one of the $R_{12}$ and $R_{13}$ may independently be a hydrogen atom, a phenyl group, or a methyl group. X may be nitrogen and Y may be oxygen.

The compound represented by Formula 1 may be any one of compounds represented by Formulae 7 or 8, Formula 7

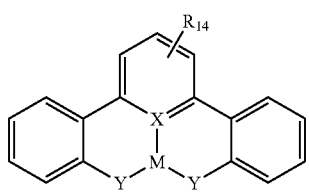

Formula 8

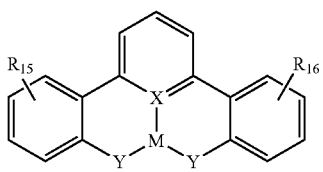

wherein $R_{14}$, $R_{15}$ and $R_{16}$ may each independently be a hydrogen atom, a cyano group, a hydroxyl group, a nitro group, a halogen atom, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, or a substituted or unsubstituted C2-C20 hetero ring group. Each one of the $R_{14}$ through $R_{16}$ may independently be a hydrogen atom, a phenyl group, or a methyl group. X may be nitrogen and Y may be oxygen. M may be beryllium, X may be nitrogen, and Y may be oxygen. The heterocycle-containing organometallic complex may be represented by Formula 9, Formula 9

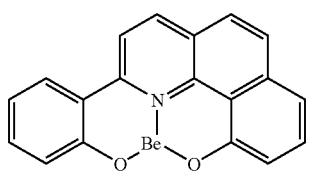

At least one of the above and other features and advantages of the present invention may be further realized by providing an organic light emitting device, including a first electrode, a second electrode, and an organic layer between the first and second electrodes, wherein the organic layer includes a substantially planar organometallic complex for a light emitting layer, the organometallic complex including a heterocyclic ligand and a bivalent metal bonded to the heterocyclic ligand. The heterocyclic ligand may include a plurality of linked ring structures that include a total of at least 17 carbon atoms and 1 heteroatom, and the linked ring structures may have substantially parallel planes.

The organometallic complex may be represented by a general Formula 1,

Formula 1

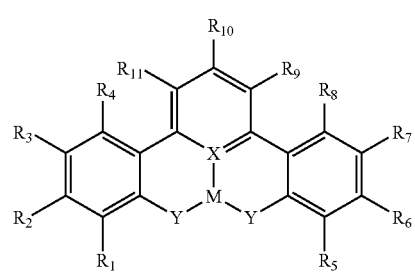

wherein $R_1$ through $R_{11}$ may each independently be a hydrogen atom, a cyano group, a hydroxyl group, a nitro group, a halogen atom, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, or a substituted or unsubstituted C2-C20 hetero ring group; M may be beryllium, magnesium, zinc, calcium, chromium, iron, cobalt, nickel, or copper; X may be nitrogen or phosphorous; and Y may be oxygen or sulfur.

The organic layer may have a multi-layered structure. The organic layer may be one or more of an electron transport layer, an electron injection layer, an electron blocking layer, an emitting layer, a hole injection layer, a hole blocking layer, and/or a hole transport layer. The organic layer may be an emitting layer including a host material and the heterocycle-containing organometallic complex. The heterocycle-containing organometallic complex may be a dopant in an amount of about 1 part to about 50 parts by weight based on 100 parts by weight of a total weight of the host material and the dopant. The organic layer may include the hole transport layer, emitting layer, and electron transport layer between the first and second electrodes. The layer may further include the hole injection layer and the electron injection layer. The layer may further include the hole blocking layer between the electron transport layer and the hole transport layer, and the emitting layer, electron transport layer, and electron injection layer include the heterocycle-containing organometallic complex. The heterocycle-containing organometallic complex may include any one of compounds represented by Formulae 2 through 8, Formula 2

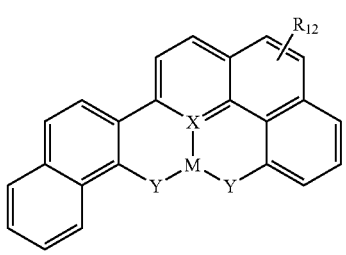

-continued

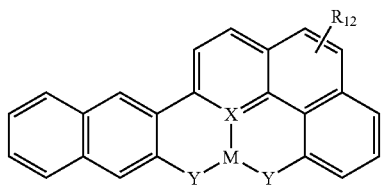

Formula 3

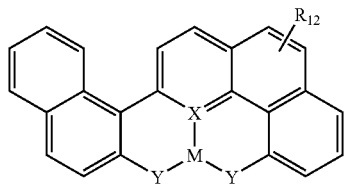

Formula 4

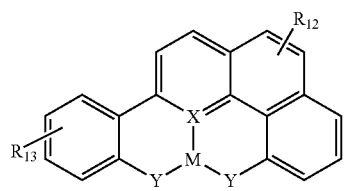

Formula 5

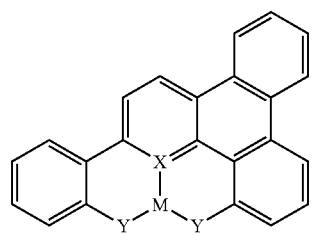

Formula 6

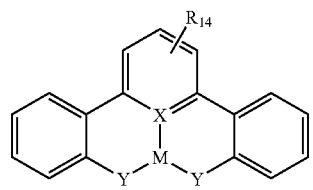

Formula 7

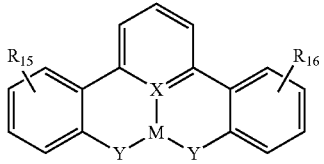

Formula 8 wherein $R_{12}$ through $R_{16}$ may each independently be a hydrogen atom, a cyano group, a hydroxyl group, a nitro group, a halogen atom, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, or a substituted or unsubstituted C2-C20 hetero ring group.

BRIEF DESCRIPTION OF THE DRAWINGS

The above and other features and advantages of the present invention will become more apparent to those of ordinary skill in the art by describing in detail exemplary embodiments thereof with reference to the attached drawings, in which:

FIGS. 1A-1C illustrate schematic cross-sectional views of light emitting diodes of organic light emitting devices according to embodiments of the present invention.

DETAILED DESCRIPTION OF THE INVENTION

Korean Patent Application No. 10-2007-0005813, filed on Jan. 18, 2007, in the Korean Intellectual Property Office, and entitled: "Heterocycle-Containing Organometallic Complex and Organic Light Emitting Device Comprising the Same," is incorporated by reference herein in its entirety.

Exemplary embodiments of the present invention will now be described more fully hereinafter. Aspects of the invention may, however, be embodied in different forms and should not be construed as limited to the embodiments set forth herein. Rather, these embodiments are provided so that this disclosure will be thorough and complete, and will fully convey the scope of the invention to those skilled in the art. In chemical formulas, like character numerals refer to like elements throughout.

A heterocycle-containing organometallic complex according to an embodiment of the present invention may include a bivalent metal and a ligand. In an implementation, the bivalent metal may be bonded to the ligand by a coordinate bond and two covalent bonds. The heterocycle-containing organometallic complex may be represented by Formula 1 below:

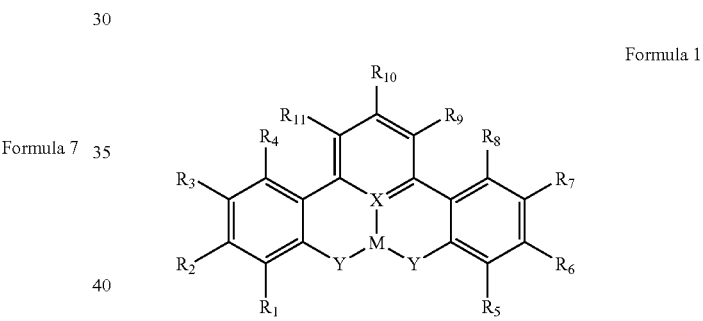

Formula 1 where $R_1$ through $R_{11}$ may each independently be a hydrogen, a halogen atom, a cyano group, a hydroxyl group, a nitro group, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, a substituted or unsubstituted C2-C20 hetero ring group, and so forth, and/or at least two of the $R_1$ through $R_{11}$ may be bound to each other to form a substituted or unsubstituted carbon ring or a hetero ring. The M may be the bivalent metal, e.g., beryllium (Be), magnesium (Mg), zinc (Zn), calcium (Ca), chromium (Cr), iron (Fe), cobalt (Co), nickel (Ni), or copper (Cu). The X may be nitrogen (N) or phosphorous (P). The Y may be oxygen (O) or sulfur (S).

For example, the heterocycle-containing organometallic complex represented by Formula 1 may be any one of the compounds represented by Formulae 2-8 below, where each one of the $R_1$ through $R_{11}$ not indicated to include a functional group, i.e., an "R" group, and/or form a cyclic structure, is a hydrogen atom.

Formula 2

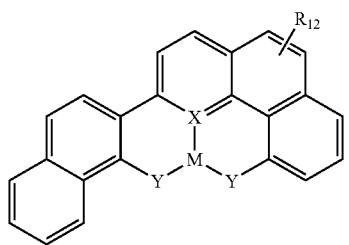

Formula 3

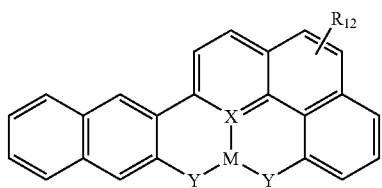

Formula 4

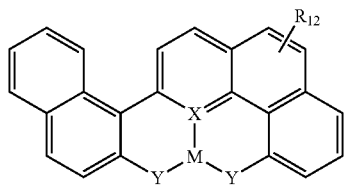

Formula 5

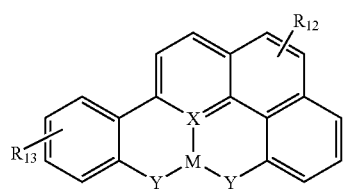

Formula 6

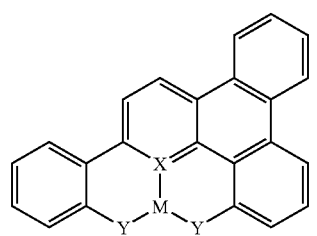

Formula 7

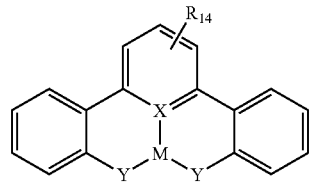

Formula 8

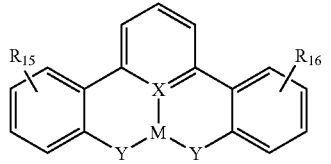

where $R_{12}$ through $R_{16}$ may each independently be a hydrogen, a halogen atom, a cyano group, a hydroxyl group, a nitro group, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, a substituted or unsubstituted C2-C20 hetero ring group, and so forth. For example, in the compounds represented by Formulae 2-8, the $R_{12}$ through $R_{16}$ may each independently be a hydrogen atom, a phenyl group, or a methyl group, X may be nitrogen, and Y may be oxygen. More specifically, the heterocycle-containing organometallic complex according to an embodiment of the present invention may be represented, for example, by Formula 9 below. However, other compounds represented by Formula 1 are not excluded from the scope of the present invention.

Formula 9

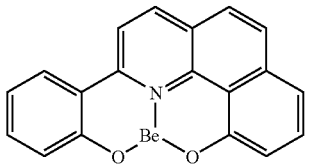

Examples of an unsubstituted C1-C20 alkyl group in Formulae 1-8 may include methyl, ethyl, propyl, isobutyl, sec-butyl, pentyl, iso-amyl, hexyl, and so forth. Examples of a substituted C1-C20 alkyl group in Formulae 1-8 may include any of the unsubstituted C1-C20 alkyl group, where at least one hydrogen atom is substituted with a halogen atom, hydrazine, hydrazone, a hydroxyl group, a nitro group, a cyano group, an amino group, an amidino group, a carboxyl group or salts thereof, a sulfonic acid or salts thereof, a phosphoric acid or salts thereof, a C1-C20 alkyl group, a C1-C20 alkenyl group, a C6-C20 aryl group, a C7-C20 arylalkyl group, a C2-C20 hetero-aryl group, or a C3-C20 hetero-arylalkyl group.

Examples of an unsubstituted C1-C20 alkoxy group in Formulae 1-8 may include a methoxy group, an ethoxy group, a phenyloxy group, a cyclohexyloxy group, a naphthyloxy group, an isopropyloxy group, a diphenyloxy group, and so forth. Examples of a substituted C1-C20 alkoxy group in Formulae 1-8 may include any of the unsubstituted C1-C20 alkoxy groups, where at least one hydrogen atom is substituted with any of the potential substituents discussed previously with respect to the substituted C1-C20 alkyl group.

The unsubstituted C6-C20 aryl group in Formulae 1-8 may refer to any aromatic group containing at least one ring, where the rings may be attached to each other by a pendant method, or may be fused with each other. Examples of the unsubstituted C6-C20 aryl group may include phenyl, naphthyl, tetrahydronaphthyl, and do forth. Examples of a substituted C6-C20 aryl group in Formulae 1-8 may include any of the unsubstituted C6-C20 aryl groups, where at least one hydrogen atom is substituted with any of the potential substituents discussed previously with respect to the substituted C1-C20 alkyl group.

The unsubstituted C7-C20 arylalkyl group in Formulae 1-8 may include any C6-C20 aryl group as defined above, where a hydrogen atoms is substituted with a lower alkyl, e.g., methyl, ethyl, propyl, and so forth. Examples of the unsubstituted C7-C20 arylalkyl group may include benzyl, phenylethyl, and so forth. Examples of a substituted C7-C20 arylalkyl group in Formulae 1-8 may include any of the unsubstituted C7-C20 arylalkyl group, where at least one hydrogen atom is substituted with any of the potential substituents discussed previously with respect to the substituted C1-C20 alkyl group.

The unsubstituted hetero-ring group in Formulae 1-8 may refer to monovalent monocyclic or bivalent bicyclic aromatic organic compounds having about 6-70 ring atoms with 1, 2, or 3 non-carbon atoms, e.g., N, O, P, and/or S, in each carbon ring. Examples of the unsubstituted hetero ring group may include thienyl, pyridyl, furyl, and so forth. Examples of a substituted hetero-ring group in Formulae 1-8 may include any of the unsubstituted hetero-ring group, where at least one hydrogen atom is substituted with any of the potential substituents discussed previously with respect to the substituted C1-C20 alkyl group.

The heterocycle-containing organometallic complex may have a substantially planar molecular structure, so molecular planes along the stacking direction may be substantially parallel to each other, as opposed to having a herringbone structure, thereby improving stability thereof. The planar structure of the heterocycle-containing organometallic complex may depend on the central metal and the substituents. Without indenting to be bound by theory, it is believed that a substantially planar molecule, i.e., the heterocycle-containing organometallic complex, may be aligned substantially uniformly along a single plane, and may also be uniformly positioned with respect to, e.g., a substrate, thereby facilitating stacking of the organometallic complexes within the single plane and among adjoining planes. Increased stacking of hetero-rings along the single plane may increase in-plane electron mobility along the stacking direction of the heterocycle-containing organometallic complex. As such, the heterocycle-containing organometallic complex according to an embodiment of the present invention may be advantageous in providing an improved material for forming a light emitting layer, thereby facilitating manufacturing of a light emitting diode (LED) having enhanced lifetime and efficiency.

An organic light emitting device including the heterocycle-containing organometallic complex in a LED according to an embodiment of the present invention may include a first electrode, a second electrode, and an organic light emitting layer including the heterocycle-containing organometallic complex represented by Formula 1 therebetween.

The light emitting layer of the organic light emitting device may have a multi-layered structure, as illustrated in FIGS. 1A-1C, and may include one or more of an electron transport layer, an electron injection layer, a hole blocking layer, an emitting layer, an electron blocking layer, a hole injection layer, and/or a hole transport layer between the first and second electrodes. For example, the light emitting layer may include the heterocycle-containing organometallic complex represented by Formula 1 in one or more of the emitting layer, electron transport layer, and/or the electron injection layer.

More particularly, as illustrated in FIG. 1A, the organic light emitting device according to an embodiment of the present invention, e.g., an organic light emitting diode display device, may include the first electrode on a substrate, the hole transport layer, emitting layer, and electron transport layer sequentially formed sequentially on the first electrode, and the second electrode on the electron transport layer. As illustrated in FIG. 1B, the organic light emitting device may have the hole injection layer, hole transport layer, emitting layer, electron transport layer, and electron injection layer formed on the first electrode, followed by positioning of the second electrode on the electron injection layer. In addition, as illustrated in FIG. 1C, the organic light emitting device may include the hole injection layer, hole transport layer, emitting layer, hole blocking layer, electron transport layer, and electron injection layer formed on the first electrode, followed by formation of the second electrode on the electron injection layer.

A method of manufacturing an organic light emitting device having a LED with a multi-layered light emitting layer illustrated in FIG. 1C is as follows.

First, the first electrode, e.g., an anode, may be formed by depositing, e.g., via sputtering, a high work-function material on the substrate. The substrate may be any suitable substrate. In implementation, the substrate may be a material exhibiting transparency, surface smoothness, and water resistance, e.g., a glass substrate or a transparent plastic substrate. The first electrode may be formed of a transparent material with a high conductivity, e.g., indium tin oxide (ITO), indium zinc oxide (IZO), tin oxide ($SnO_2$), zinc oxide (ZnO), and so forth.

The hole injection layer may be deposited by, e.g., vacuum thermal deposition or spin coating, on the first electrode. The hole injection layer may be formed of, e.g., copper phthalocyanine (CuPc) represented by the formula below or starburst type amines, such as 4,4',4"-tris(N-carbazolyl)triphenylamine (TCTA) and 4,4',4"-tris(3-methylphenyl)phenylamino]-triphenylamine (m-MTDATA), represented by the formulae below, IDE406 (Idemitsu Co.), and so forth.

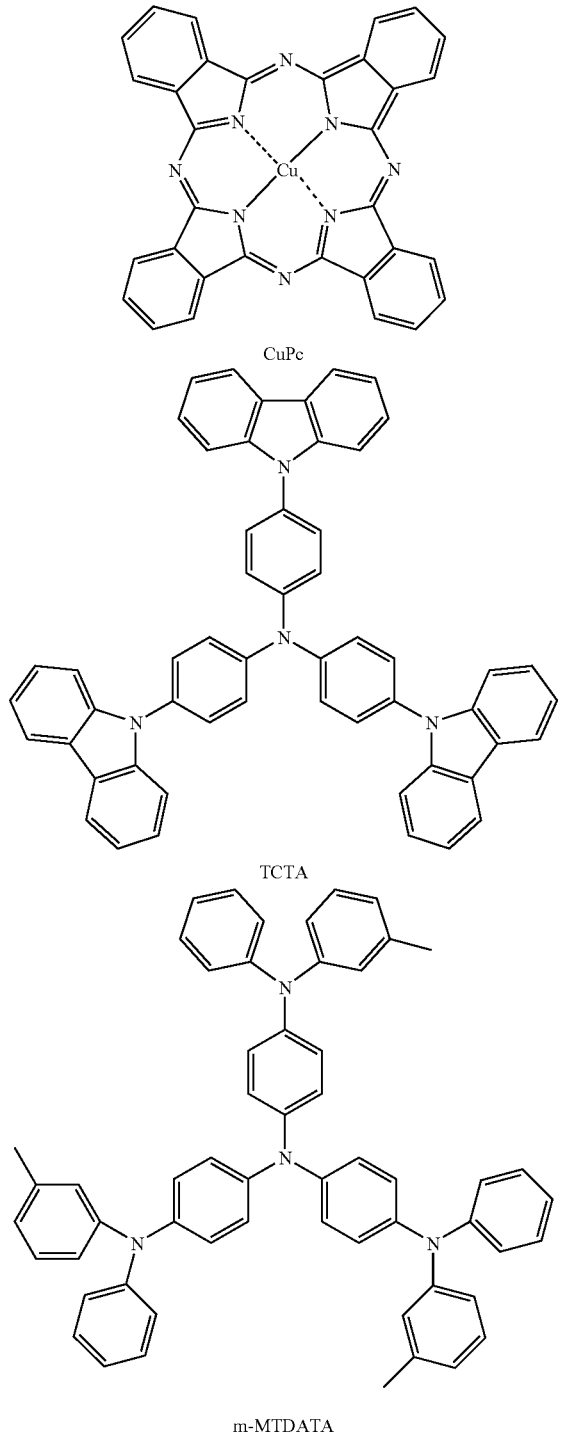

The hole transport layer may be deposited by, e.g., vacuum thermal deposition or spin coating, on the hole injection layer. The hole transport layer may be formed of, e.g., 4,4'-bis(N-(3-methylphenyl)-N-phenylamino]biphenyl (TPD) and N,N'-di(naphthalene-1-yl)-N,N'-diphenyl benzidine (α-NPD), represented by the formulae below, IDE320 (Idemitsu Co.), and so forth.

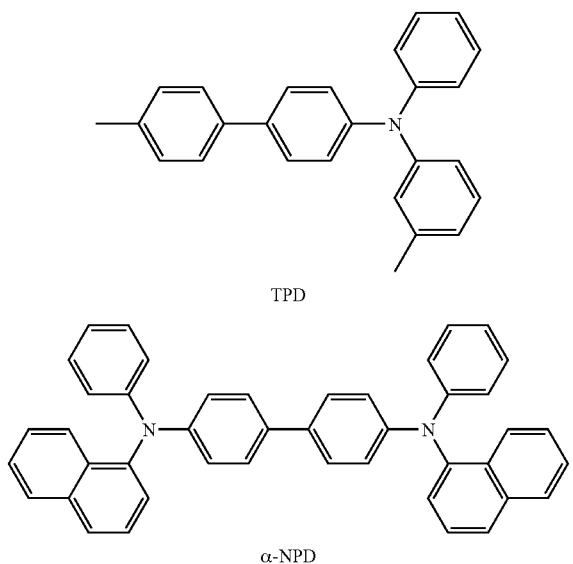

TPD

α-NPD

The emitting layer may be formed on the hole transport layer by, e.g., vacuum thermal deposition, and may include the heterocycle-containing organometallic complex represented by Formula 1 as a main component or as a dopant. If the heterocycle-containing organometallic complex represented by Formula 1 is used as a dopant, a host material, e.g., 4,4'-N,N'-dicarbazol-biphenyl (CBP), tricholorobenzene (TCB), 4,4'-biscarbazolyl-2,2'-dimethylbiphenyl (dmCBP), 8-hydroxy-quinolinato lithium (Liq), 2,2',2''-(1,3,5-benzenetriyl)tris(1-phenyl-1H-benzimidazole) (TPBI), aluminum (III) bis(2-methyl-8-quinolinate)4-phenylphenolate (Balq), bathocuproine (BCP), TCTA, SDI-BH-18, SDI-BH-19, SDI-BH-22, and SDI-BH-23, represented by the following formulae, may be used.

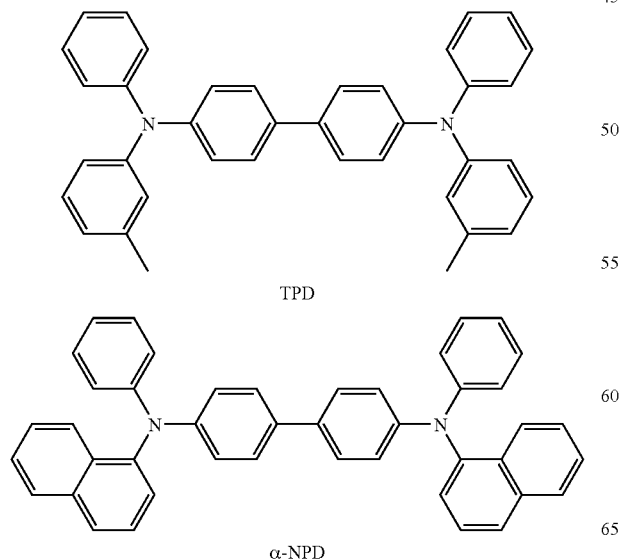

TPD

α-NPD

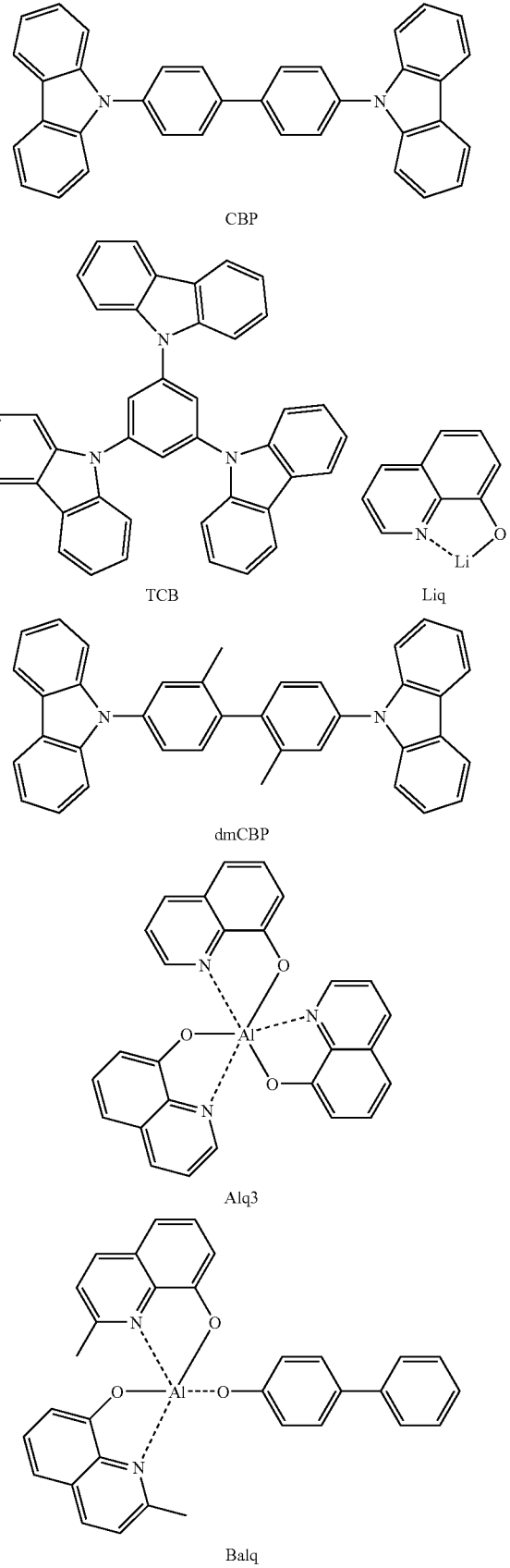

CBP

TCB

Liq dmCBP

Alq3

Balq

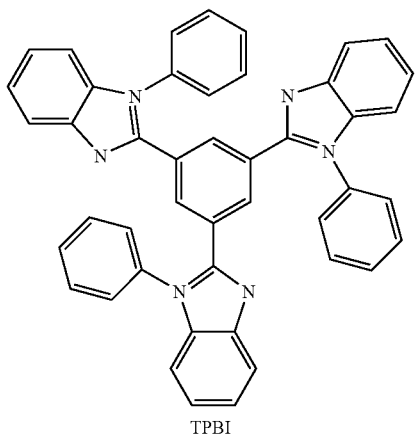

TPBI

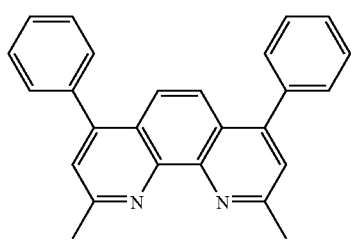

BCP

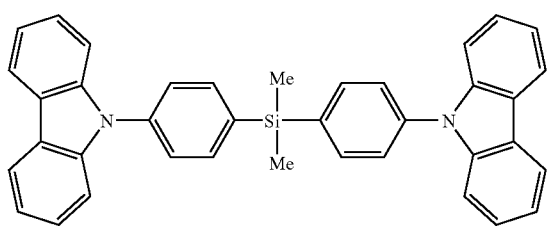

SDI-BH-18

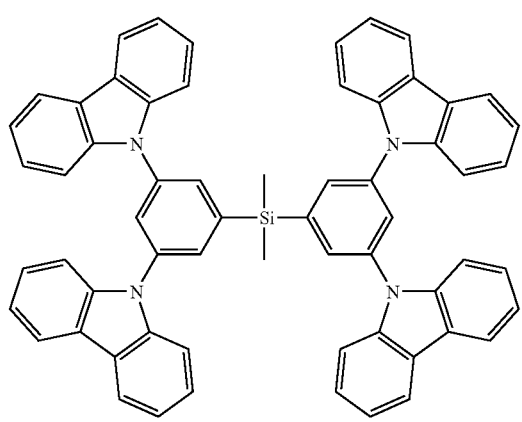

SDI-BH-19

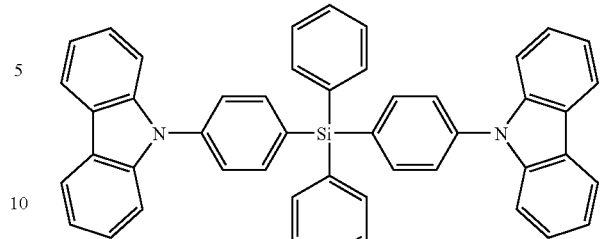

SDI-BH-22

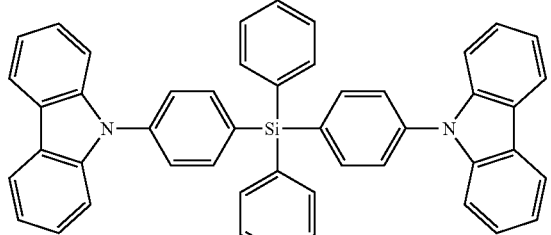

SDI-BH-23

When the heterocycle-containing organometallic complex represented by Formula 1 is used as a dopant, the heterocycle-containing organometallic complex may be used in an amount of about 1 part to about 50 parts by weight based on about 100 parts by weight of a total weight of the host material and the heterocycle-containing organometallic complex.

The hole blocking layer may be formed on the emitting layer by, e.g., vacuum deposition or spin coating, of a material having an electron transporting ability and a higher ionization potential than the material of the emitting layer. Examples of suitable materials for forming the hole blocking layer may include Balq, BCP, TPBI, and so forth.

The electron transport layer may be formed on the hole blocking layer by, e.g., vacuum deposition or spin coating, of the heterocycle-containing organometallic complex represented by Formula 1 or of a quinoline derivative, e.g., tris(8-quinolinolate)aluminum ($Alq_3$).

The electron injection layer may be formed on the electron transport layer of the heterocycle-containing organometallic complex represented by Formula 1 and/or of, e.g., lithium fluoride (LiF), sodium chloride (NaCl), cesium fluoride (CsF), lithium oxide ($Li_2O$), barium oxide (BaO), Liq, and so forth. The metal material may be, e.g., lithium (Li), magnesium (Mg), aluminum (Al), aluminum lithium (Al—Li), calcium (Ca), magnesium indium (Mg—In), magnesium silver (Mg—Ag), and so forth. If the organic light emitting device is a top-emitting device, the second electrode may be formed of a transmissive material, e.g., ITO or IZO.

The organic light emitting device may further include one or two interlayers on either one of the first electrode, hole injection layer, hole transport layer, emitting layer, hole blocking layer, electron transport layer, electron injection layer, and/or second electrode. The organic light emitting device may also include an electron blocking layer.

EXAMPLE

An organic light emitting layer was prepared according to an embodiment of the present invention, i.e., an organic light emitting layer including the heterocycle-containing organometallic complex represented by Formula 1, and compared to a conventional organic light emitting layer, i.e., an organic light emitting layer without the heterocycle-containing organometallic complex represented by Formula 1.

Example 1

A heterocycle-containing organometallic complex represented by Compound 2 was synthesized according to the reaction scheme below.

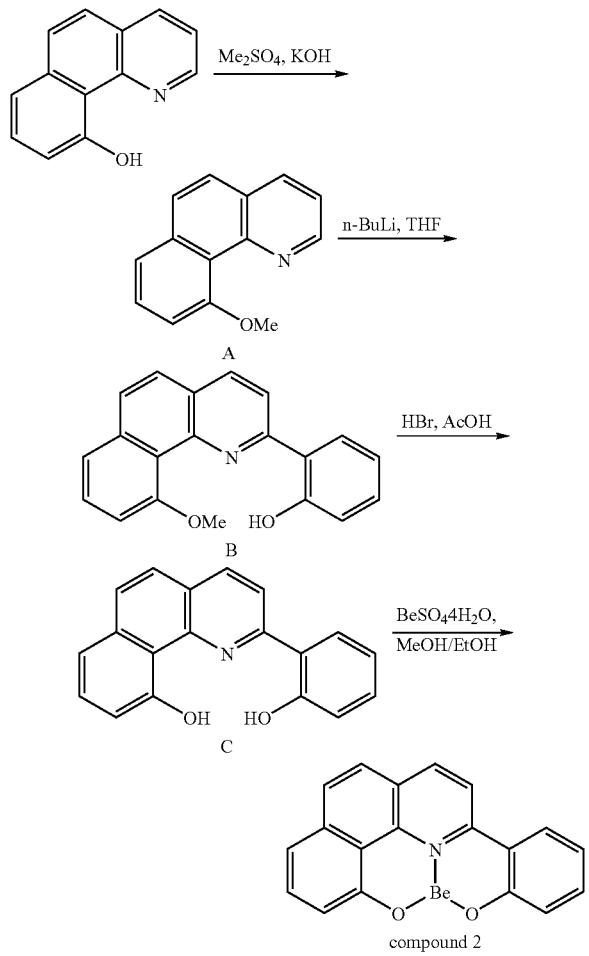

More specifically, 3 g of Compound C were dissolved in 70 ml of EtOH/MeOH (1/1) to form a mixture, followed by adding 1.8 g of $BeSO_4 \cdot 4H_2O$ dissolved in 180 ml of $H_2O$ into the mixture. Next, pH of the mixture was adjusted to be 10 by adding NaOH (1 N). Subsequently, the mixture was stirred at room temperature for 5 hours to produce a yellow solid product. The yellow solid product was filtered and washed using $H_2O$ and an EtOH/MeOH solution to obtain Compound 2. An 1H NMR (DMSO-d6, 400 MHz) spectroscopic analysis of Compound 2 showed δ (ppm), 8.55(1H, d), 8.36(1H, d), 8.09(1H, d), 7.81(1H, d), 7.74(1H, d), 7.53(1H, t), 7.30(1H, m), 7.19(1H, d), 6.92(1H, d), 6.83(1H, d), 6.71(1H, t). Compound 2 was substantially planar, i.e., compound 2 exhibited an angle of 5.98° with respect to a plane of compound 2.

Once compound 2 was formed, an organic light emitting device having a substantially same structure as illustrated in FIG. 1B was manufactured, i.e., m-MTDATA (750 angstroms)/α-NPD(150 angstroms)/DSA(300 angstroms):TPBe (3%)/$Alq_3$(200 angstroms)/Compound 2(50 angstroms)/Al (3000 angstroms). More specifically, 15 Ω/$cm^2$ (1200 angstroms) Corning ITO glass substrate was cut to a size of 50 mm×50 mm×0.7 mm, ultrasonically washed using isopropyl alcohol and pure water for 5 minutes each, respectively, and then washed with UV ozone for 30 minutes in order to form the anode. Next, m-MTDATA was vacuum deposited on the anode to form a hole injection layer having a thickness of 750 angstroms. Subsequently, α-NPD was vacuum deposited on the hole injection layer to form a hole transport layer having a thickness of 150 angstroms. Next, DSA used as a host and 3% of TPBe used as a dopant were vacuum deposited on the hole transport layer to form an emitting layer having a thickness of 300 angstroms. Then, $Alq_3$ was vacuum deposited on the emitting layer to form an electron transport layer having a thickness of 200 angstroms. Compound 2 was vacuum deposited on the electron transport layer to a thickness of 50 angstroms to form an electron injection layer, followed by vacuum deposition of aluminum to a thickness of 3000 angstroms to form the cathode.

Comparative Example 1

An organic light emitting device was formed according to a substantially same method as Example 1, with the exception of using 50 angstroms of Liq, instead of Compound 2, in order to form the electron injection layer.

Evaluation: The organic light emitting devices of Example 1 and Comparative Example 1 were compared in terms of current-voltage properties, luminance properties, efficiency properties, and power consumption. The current-voltage properties were measured while applying a forward bias to each device and using Keithley 238. The luminance properties, efficiency properties, and power consumption were measured using a spectracolorimeter (PhotoResearch PR650). Comparison results are reported in Table 1 below.

TABLE 1

| | Driving Voltage (mV) | Current Density (mA/$cm^2$) | Luminance (cd/$m^2$) | Current Efficiency (cd/A) | Power Efficiency (lm/W) |
|---|---|---|---|---|---|
| Example 1 | 6000 | 11.20025 | 548 | 4.89 | 2.56184 |
| | 8000 | 114.89 | 6216 | 5.41 | 2.12466 |
| Comparative Example 1 | 6500 | 13.32875 | 701 | 5.26 | 2.54194 |
| | 8500 | 83.1425 | 5325 | 6.4 | 2.36716 |

As illustrated in Table 1 above, a lower driving voltage may be used for the organic light emitting of Example 1, as compared to the driving voltage of the Comparative Example 1, thereby reducing current density and improving power efficiency thereof. Further, at higher driving voltages, even though current density of the organic light emitting device of Example 1 may increase, luminance thereof may be substantially higher than luminance of the organic light emitting device of Comparative Example 1. Accordingly, the organic light emitting device including the organic light emitting layer with the heterocycle-containing organometallic complex according to an embodiment of the present invention may have excellent electron transporting ability, high efficiency, low driving voltage, improved luminance, and enhanced lifetime.

Embodiments of the present invention have been disclosed herein with reference to the accompanying drawings, in which exemplary embodiments of the invention were illustrated. Aspects of the invention may, however, be embodied in different forms and should not be construed as limited to the embodiments set forth herein. Rather, these embodiments are provided so that this disclosure will be thorough and complete, and will fully convey the scope of the invention to those skilled in the art.

In the figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present.

Exemplary embodiments of the present invention have been disclosed herein, and although specific terms are employed, they are used and are to be interpreted in a generic and descriptive sense only and not for purpose of limitation. Accordingly, it will be understood by those of ordinary skill in the art that various changes in form and details may be made therein without departing from the spirit and scope of the present invention as set forth in the following claims.

What is claimed is:

1. An organic light emitting device, comprising:
    a first electrode;
    a second electrode; and
    an organic layer between the first and second electrodes, wherein the organic layer includes a heterocycle-containing organometallic complex represented by a general Formula 1:

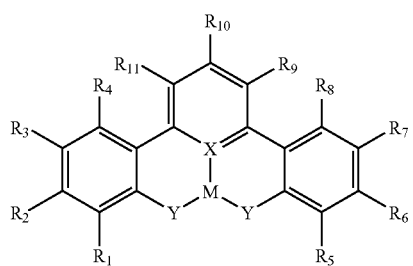

Formula 1 wherein each of $R_1$ through $R_{11}$ is a hydrogen atom, a cyano group, a hydroxyl group, a nitro group, a halogen atom, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, or a substituted or unsubstituted C2-C20 hetero ring group; M is beryllium, magnesium, zinc, calcium, chromium, iron, cobalt, nickel, or copper; X is nitrogen or phosphorous; and Y is oxygen or sulfur.

2. The organic light emitting device as claimed in claim 1, wherein the organic layer has a multi-layered structure.

3. The organic light emitting device as claimed in claim 2, wherein the organic layer includes one or more of an electron transport layer, an electron injection layer, an electron blocking layer, an emitting layer, a hole injection layer, a hole blocking layer, and/or a hole transport layer.

4. The organic light emitting device as claimed in claim 3, wherein the organic layer is an emitting layer including a host material and the heterocycle-containing organometallic complex.

5. The organic light emitting device as claimed in claim 4, wherein the heterocycle-containing organometallic complex is a dopant in an amount of about 1 part to about 50 parts by weight based on 100 parts by weight of a total weight of the host material and the dopant.

6. The organic light emitting device as claimed in claim 5, wherein the organic layer includes the hole transport layer, emitting layer, and electron transport layer between the first and second electrodes.

7. The organic light emitting device as claimed in claim 6, wherein the organic layer further comprises the hole injection layer and the electron injection layer.

8. The organic light emitting device as claimed in claim 6, wherein the organic layer further comprises the hole blocking layer between the electron transport layer and the hole transport layer, and
    the emitting layer, electron transport layer, and electron injection layer include the heterocycle-containing organometallic complex.

9. The organic light emitting device as claimed in claim 1, wherein the complex represented by Formula 1 is any one of compounds represented by Formulae 2 through 6,

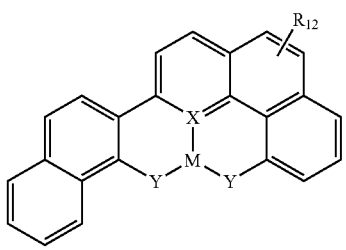

Formula 2

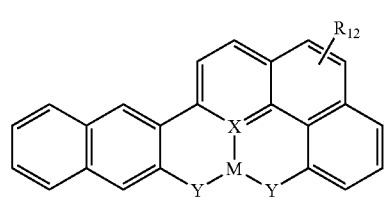

Formula 3

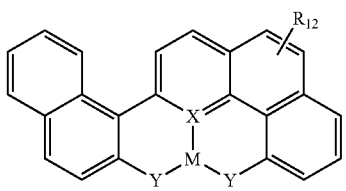

Formula 4

Formula 5

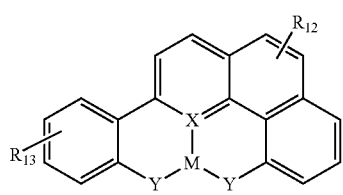

Formula 6

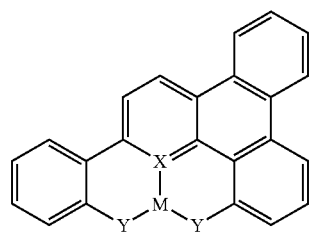

wherein each one of $R_{12}$ and $R_{13}$ is a hydrogen atom, a cyano group, a hydroxyl group, a nitro group, a halogen atom, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, or a substituted or unsubstituted C2-C20 hetero ring group.

10. The organic light emitting device as claimed in claim 9, wherein each one of the $R_{12}$ and $R_{13}$ is a hydrogen atom, a phenyl group, or a methyl group.

11. The organic light emitting device as claimed in claim 9, wherein X is nitrogen and Y is oxygen.

12. The organic light emitting device as claimed in claim 1, wherein the compound represented by Formula 1 is any one of compounds represented by Formulae 7 or 8, Formula 7

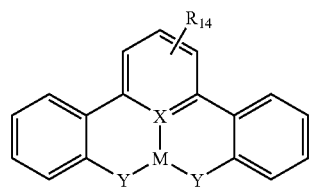

Formula 8

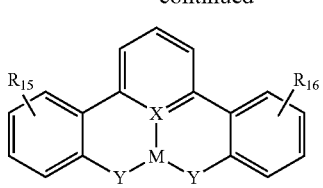

wherein each of $R_{14}$, $R_{15}$ and $R_{16}$ is a hydrogen atom, a cyano group, a hydroxyl group, a nitro group, a halogen atom, a substituted or unsubstituted C1-C20 alkyl group, a substituted or unsubstituted C1-C20 alkoxy group, a substituted or unsubstituted C6-C20 aryl group, a substituted or unsubstituted C7-C20 arylalkyl group, a substituted or unsubstituted C2-C20 alkylalkoxy group, a substituted or unsubstituted C7-C20 arylalkoxy group, a substituted or unsubstituted C6-C20 arylamino group, a substituted or unsubstituted C1-C20 alkylamino group, a substituted or unsubstituted C1-C20 alkoxyamino group, or a substituted or unsubstituted C2-C20 hetero ring group.

13. The organic light emitting device as claimed in claim 12, wherein each one of the $R_{14}$ through $R_{16}$ is a hydrogen atom, a phenyl group, or a methyl group.

14. The organic light emitting device as claimed in claim 12, wherein X is nitrogen and Y is oxygen.

15. The organic light emitting device as claimed in claim 1, wherein the M is beryllium, X is nitrogen, and Y is oxygen.

16. The organic light emitting device as claimed in claim 15, wherein the heterocycle-containing organometallic complex is represented by Formula 9.

Formula 9

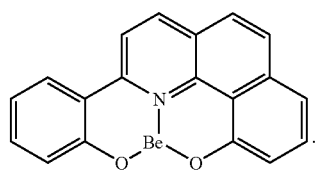

17. The organic light emitting device as claimed in claim 1, wherein at least two of the $R_1$ through $R_{11}$ are bound to each other to form a ring.

* * * * *